United States Patent [19]  [11] 4,278,516
Zaiko et al.  [45] Jul. 14, 1981

[54] METHOD FOR THE PREPARATION OF 2-FLUORO-4-MONOBROMOMETHYL-BIPHENYL

[75] Inventors: Edward J. Zaiko; Paul F. Ranken, both of Baton Rouge, La.

[73] Assignee: Ethyl Corporation, Richmond, Va.

[21] Appl. No.: 53,060

[22] Filed: Jun. 28, 1979

[51] Int. Cl.³ .......................... B07J 1/10; C07C 25/18
[52] U.S. Cl. ......................... 204/158 HA; 260/465 G; 260/465 D; 562/492; 570/129
[58] Field of Search ............ 260/649 F; 204/158 HA; 570/129

[56] References Cited

U.S. PATENT DOCUMENTS 3,755,427  8/1973  Adams et al. ................ 260/649 F X
3,959,364  5/1976  Armitage et al. ................ 260/515 R

FOREIGN PATENT DOCUMENTS 53-116352 10/1978 Japan.

OTHER PUBLICATIONS

Engel et al., Chemical Abstracts, vol. 83, 96748n (1975).

*Primary Examiner*—Dolph H. Torrence
*Attorney, Agent, or Firm*—Donald L. Johnson; John F. Sieberth

[57] ABSTRACT

2-(2-Fluoro-4-biphenylyl)propionic acid is prepared from 2-amino-4-methyl-biphenyl via a series of novel intermediates. In particular 2-amino-4-methylbiphenyl is converted to 2-fluoro-4-methylbiphenyl, the methyl group is brominated to form 2-fluoro-4-monobromomethylbiphenyl which is transformed into 2-(2-fluoro-4-biphenylyl)acetonitrile. This acetonitrile is then converted to fluorbiprofen via the corresponding propionitrile or it may be converted into fluorbiprofen via the intermediate ethyl-2-(2-fluoro-4-biphenylyl)-2-cyanopropionate.

4 Claims, No Drawings

METHOD FOR THE PREPARATION OF 2-FLUORO-4-MONOBROMOMETHYLBIPHENYL

This invention relates to a process for the preparation of 2-(2-fluoro-4-biphenylyl)propionic acid, to novel intermediates in the reaction sequence and to processes for the preparation of these novel intermediates.

BACKGROUND

The compound 2-(2-fluoro-4-biphenylyl)propionic acid—known as fluorbiprofen—is a well known drug which possesses desirable anti-inflammatory, analgesic and anti-pyretic properties. Fluorbiprofen and methods for its preparation are disclosed in U.S. Pat. Nos. 3,755,427 and 3,959,364 both assigned to the Boots Company, Ltd. The former discloses a method for its preparation by reacting an ester of the appropriate substituted 4-biphenylyl acetic acid with diethyl carbonate to give a malonic ester, methylating the sodium derivative of this ester, hydrolyzing the ester, and then decarboxylating the resulting acid. The latter patent discloses a process for the preparation of aryl propionic acids—including fluorbiprofen—which comprises reaction of a Grignard compound, obtained from an aryl bromide and magnesium with a lithium, sodium, magnesium or calcium salt of 2-bromopropionic acid, followed by acidification. Japanese Kokai No. 53-116,352 (Oct. 11, 1978) also discloses a method for the preparation of fluorbiprofen by decarboxylation and hydrolysis of 2-carboalkoxy-2-(2-fluoro-4-biphenylyl)propionitrile.

Because of the beneficial properties of fluorbiprofen, novel methods for its preparation are welcomed by the art. Such is provided by the present invention.

THE INVENTION

According to this invention 2-(2-fluoro-4-biphenylyl)propionic acid is prepared by reacting a mixture of 2-amino-4-methylbiphenyl, a fluorodizing and a diazotizing agent (e.g. NH$_4$F.HF and NaNO$_2$) to form 2-fluoro-4-methylbiphenyl, reacting the 2-fluoro-4-methylbiphenyl with N-bromosuccinimide or bromine under irradiation with light to form 2-fluoro-4-monobromomethylbiphenyl, reacting the 2-fluoro-4-monobromomethylbiphenyl with an alkali metal cyanide (preferably by refluxing in ethanol and water) to form 2-(2-fluoro-4-biphenylyl)acetonitrile, reacting a mixture of this acetonitrile, a dialkyl carbonate, an alkali metal alkoxide and an alcohol, and then adding methyl bromide and heating this mixture to form 2-(2-fluoro-4-biphenylyl)propionitrile, reacting a mixture of said propionitrile and an alkali metal hydroxide in an aqueous-organic solvent to form 2-(2-fluoro-4-biphenylyl)propionic acid. Also disclosed herein are the novel intermediates
2-(2-fluoro-4-biphenylyl)acetonitrile,
2-fluoro-4-monobromomethylbiphenyl,
2-fluoro-4-methylbiphenyl,
and ethyl-2-(2-fluoro-4-biphenylyl)-2-cyanopropionate. Fluorbiprofen is also prepared by way of this cyanopropionate intermediate.

The reaction disclosed herein is depicted generally by the following scheme:

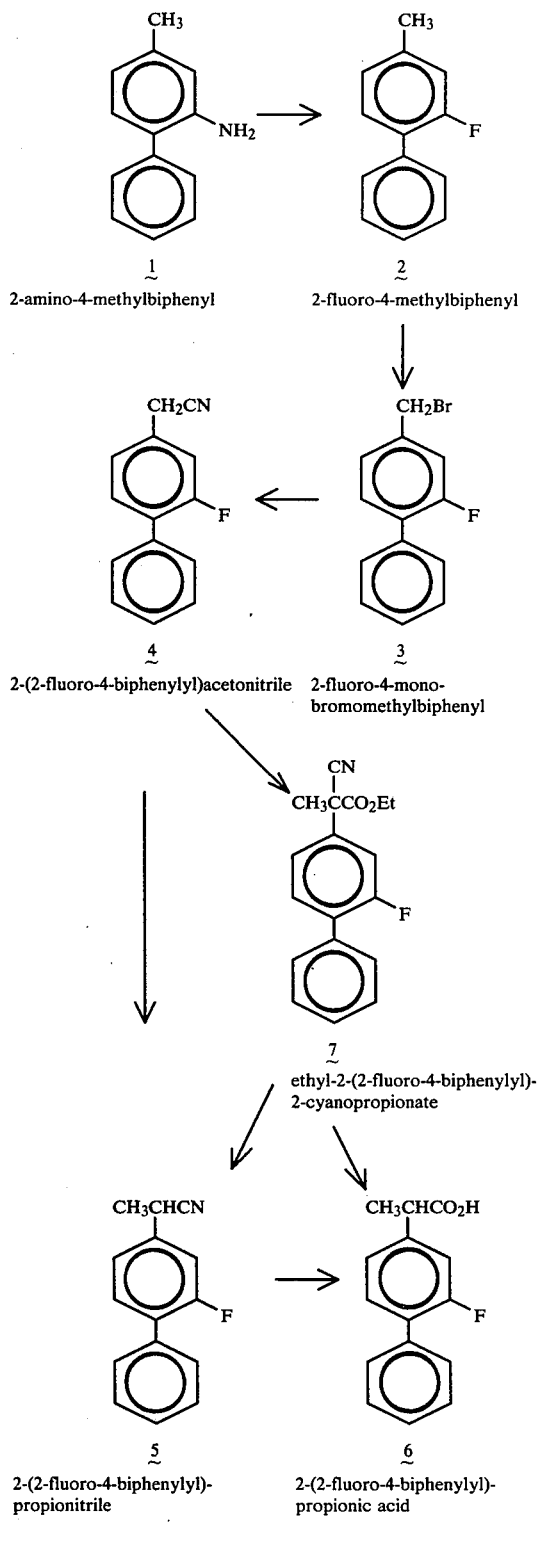

1
2-amino-4-methylbiphenyl 2
2-fluoro-4-methylbiphenyl 4
2-(2-fluoro-4-biphenylyl)acetonitrile 3
2-fluoro-4-monobromomethylbiphenyl 7
ethyl-2-(2-fluoro-4-biphenylyl)-2-cyanopropionate 5
2-(2-fluoro-4-biphenylyl)-propionitrile 6
2-(2-fluoro-4-biphenylyl)-propionic acid Preparation of the 2-amino-4-methylbiphenyl starting meterial is described by B. L. Hollingsworth and V. Petrow in the *Journal of the Chemical Society*, pp. 3771 through 3773, 1961. The diazonium salt produced by the diazotization of 4-amino-3-nitrotoluene is condensed with benzene in the presence of alkali to produce 4-methyl-2-nitrophenyl. The nitro group at the 2- position is subsequently reduced by a traditional method to obtain 2-amino-4-methylbiphenyl.

Each step of the present process is now described. The aminobiphenyl (1) is converted to the fluoride by means of suitable fluorodizing and diazotizing agents, preferably by way of the diazonium salt in 70% hydrofluoric acid. This may be accomplished by the portional addition of a diazotizing agent, e.g. sodium nitrite, potassium nitrite, nitrous anhydride, nitrous acid, a nitrosyl halide, with sodium nitrite being preferred, to a solution of the amino-biphenyl, $NH_4F \cdot HF$ and 70% HF so that the temperature does not rise above 5° C. The mixture is then stirred for about 15 minutes at a sufficiently low temperature for the product to form, generally between about −20° C. and 15° C. The diazonium fluoride is then decomposed by heat. It has been found that adding one equivalent of ammonium fluoride to the reaction mixture makes workup easier because less of the tarry by-product precipitates. This technique is described in U.S. Pat. No. 4,075,252 issued Feb. 12, 1978. Along with the fluoride, about 5% of the corresponding hydroxy compound is found in the crude product. This by-product is only partially removed on distillation and is unaffected by an aqueous NaOH wash, but it is completely removed when a petroleum ether solution of the crude product is passed through a short column of silica gel. On a small scale it was found that after the silica gel treatment the pure fluoride was obtained after evaporation of the solvent. However, on a larger scale, although silica gel removed all of the hydroxy compounds, some high boiling material was still present by GC analysis. Therefore in order to obtain the pure fluoride a subsequent distillation was required. Other methods of fluorination at the 2-position, e.g. the Balz-Schiemann reaction, may also be used. In that reaction, the aminobiphenyl is reacted with sodium nitrite and fluoroboric acid to produce the diazonium fluoroborate which is subsequently heated for thermal decomposition in the presence of powdered copper to produce 2-fluoro-4-methylbiphenyl (2).

The 2-fluoro-4-methylbiphenyl obtained from the first step is then reacted with a halogenating agent such as N-bromosuccinimide, bromine or chlorine in a solvent such as ethylene dibromide, carbon tetrachloride, cyclohexane, or benzene under irradiation with light or in the presence of a free radical former such as a peroxide in order to produce 2-fluoro-4-halomethylbiphenyl, preferably the bromomethylbiphenyl (3). It has been found that photo-initiated bromination with either molecular bromine or N-bromosuccinimide (NBS) in refluxing carbon tetrachloride solution gives higher and more reproducible conversions to the monobromide. Photo-initiated bromination also occurs without solvent (i.e. with $Br_2$ at 150° C.), however, more of the dibromide is formed in this reaction.

The 2-(2-fluoro-4-biphenylyl)acetonitrile intermediate (4) is produced by reacting the 2-fluoro-4-halomethylbiphenyl with an alkali metal cyanide such as sodium cyanide or potassium cyanide in a mixed solvent of water and an organic compound such as ethanol or dioxane at elevated temperatures under reflux conditions. Since it has been found impractical to separate the monohalide from the reaction mixture, the entire crude halogenated product was refluxed in aqueous ethanol containing sodium cyanide to convert the monohalide to the nitrile.

The acetonitrile (4) is converted to the 2-substituted propionitrile by reacting a mixture of the acetonitrile, a dialkyl carbonate, an alkali metal alkoxide and an alcohol, and then adding methyl bromide and heating the mixture to form the propionitrile (5). Preferably this is accomplished by adding a solution of sodium ethoxide in ethanol under a nitrogen atmosphere to a solution of the acetonitrile and diethyl carbonate. The mixture is then heated so that the ethanol is distilled while additional diethyl carbonate is added to prevent the product from precipitating. When the temperature reaches approximately 120° C. the reaction mixture is then cooled to between about 10° and about 35° C. and ethanol is added. Methyl bromide is then added as a liquid and the reaction is kept in the range of from about 10° to about 35° C. for about an hour and then refluxed for about another hour. Initially, the ethyl-2-(2-fluoro-4-biphenyl)-2-cyanopropionate (7) was prepared by carboethoxylation of the nitrile with diethyl carbonate and sodium ethoxide, followed by methylation with dimetyl sulfate. Starting with pure nitrile (4) the cyanopropionate (7) was obtained as a high boiling liquid in 75% yield. However, it was found that if excess base were present this material could be converted to the propionitrile (5) by diluting the reaction mixture with ethanol and refluxing it for about one to two hours. The yield of the propionitrile (5) is comparable to that of the cyanopropionate (7) and it is far easier to distill since it is a lower boiling compound. It was also found that methyl bromide is an equally effective methylating agent in this reaction and furthermore is less expensive. The conversion of the acetonitrile (4) to the propionitrile (5) works equally well with starting propionitrile of a purity typical of that obtained in the present process.

The propionitrile (5) may be easily hydrolyzed in high yield to fluorbiprofen (6) with sodium hydroxide in a 1:1 methanol-water mixture. The purity of the crude hydrolysis product depends on the purity of the nitrile. Pure fluorbiprofen can be obtained by recrystallization from heptane containing 5% ethanol.

However, in an alternate reaction the cyanopropionate (7) may be prepared by carboethoxylation of the nitrile (4) with a dialkyl carbonate such as diethyl carbonate and an alkali metal alkoxide such as sodium ethoxide, followed by methylation with a methylating agent such as methyl bromide or dimethyl sulfate. The cyanopropionate is then converted into the propionitrile (5) by reacting with an alkali metal alkoxide and an alcohol such as those above. Alternatively, the cyanopropionate may be hydrolyzed under either acidic or basic conditions in water to form the product fluorbiprofen.

The following examples will serve to illustrate the specific embodiments of the present invention.

EXAMPLE 1

Preparation of 4-Methyl-2-nitrobiphenyl

The subject compound was prepared following a modification of a procedure described by Hollingsworth and Petrow in the *Journal of the Chemical Society*, pp. 3771–3773, 1961. To a cooled (ice-salt bath) suspension of 76 g (0.50 mol) of 4-methyl-2-nitroaniline in 150 ml of concentrated HCl and 100 ml of $H_2O$ was added dropwise and with mechanical stirring a solution of 38 g (0.55 mol) of $NaNO_2$ in 50 ml of $H_2O$. The addition rate was adjusted so that the temperature of the reaction mixture did not rise above 5° C. (about 45 minutes). The reaction mixture was stirred for 15 minutes at 0° C. (all temperatures hereinafter measured on the centigrade scale) filtered, and then poured into one liter of benzene which had been cooled to 6°. While the resulting two phase system was cooled with an ice bath and stirred vigorously (mechanical stirrer), a solution of 160 g (1.2 mol) of NaOAc in 400 ml of H$_2$O was added over a period of one hour. After the addition was complete, the reaction mixture was stirred at 6° for 5 hours and then at 25° for 14 hours. An aqueous solution (150 ml) containing 75 g (1.9 mol) of NaOH was then added to allow the layers to separate. The organic phase was washed with H$_2$O, dried over MgSO$_4$, and concentrated to leave a dark red liquid. This material was distilled at reduced pressure to give, after 2.6 L g of a forerun which consisted mainly of starting material, 44 g (41%) of 4-methyl-2-nitrobiphenyl (bp.140°–150° at 0.05 mm).

EXAMPLE 2

Preparation of 2-amino-4-methylbiphenyl (1)

A solution of 44 g (0.21 mol) of 2-nitro-4-methylbiphenyl prepared in Example 1 in 250 ml of ethanol was hydrogenated over 3.0 g of 5% palladium on carbon in a Parr shaker. The uptake of hydrogen stopped after 45 minutes, and the reaction mixture was filtered and concentrated to give 37 g (97%) of 2-amino-4-methylbiphenyl as a brown liquid. This material was distilled through a 15 cm Vigreaux column to give 33 g (87%) of pure 2-amino-4-methylbiphenyl as a colorless liquid, which turned brown on standing.

EXAMPLE 3

Preparation of 2-fluoro-4-methylbiphenyl (2)

To a cold (ice-salt bath) solution of 21.3 g (0.115 mol) of 2-amino-4-methyl biphenyl (prepared in Example 2) and 6.5 g (0.11 mol) of NH$_4$F.HF and 75 g of 70% HF (2.6 mol) was portion-wise added 8.9 g (0.13 mol) of NaNO$_2$ so that the temperature of the reaction mixture did not rise above 5°. This addition took approximately 40 minutes. The reaction mixture was allowed to stir at 0° for 15 minutes thereafter, and then the cooling bath was removed and stirring continued. The temperature rose to 15° after 20 minutes and then to 60° over a subsequent 25 minute period during which time nitrogen was evolved. The reaction mixture was cooled in an ice bath and extracted three times with petroleum ether. This organic extract was washed successfully with water, aqueous NaHCO$_3$, and H$_2$O and then dried over MgSO$_4$ which, after concentration left 18.8 g of dark red liquid. Subsequent analysis of this material by gas chromatography showed the fluoride compound present at about 90% by weight and about 6% by weight of the corresponding hydroxy compound. A solution of the crude product in petroleum ether was passed through a short column of silica gel. Removal of the solvent at reduced pressure left 16.6 g of pure 2-fluoro-4-methylbiphenyl (78%) as a colorless liquid.

EXAMPLE 4

Preparation of 2-fluoro-4-monobromomethylbiphenyl (3)

A solution of 19.2 g (0.103 mol) of 2-fluoro-4-methylbiphenyl and 16 g (0.09 mol) of N-bromosuccinimide (NBS) dissolved in 60 ml of CCl$_4$ was refluxed under irradiation from a sunlamp. After the initial 1 to 2 minute period of heating by the sunlamp and heating mantle the reaction became self-sustaining and the mantle was removed for the duration of the reaction (5–10 minutes) The resulting reaction mixture was filtered, washed with H$_2$O, dried over MgSO$_4$, and then concentrated to leave 26.2 g of yellow liquid. NMR analysis showed this material to contain the starting methylbiphenyl, the monobromide and the dibromide in a ratio of 21:71:7.

EXAMPLE 5

Preparation of 2-fluoro-4-monobromomethylbiphenyl (3)

In this instance one equivalent of Br$_2$ was added dropwise to a refluxing solution of 2-fluoro-4-methylbiphenyl and CCl$_4$ while being irradiated with a sunlamp. NMR analysis showed the ratio of starting material:monobromide:dibromide to be 21:67:12.

EXAMPLE 6

Preparation of 2-fluoro-4-monobromomethylbiphenyl (3)

In a similar experiment 0.8 equivalent of Br$_2$ was added dropwise to a refluxing solution of 2-fluoro-4-methylbiphenyl (2) and CCl$_4$. NMR analysis showed the ratio of starting material:monobromide:dibromide to be 31:61:8.

EXAMPLE 7

Preparation of 2-fluoro-4-monobromomethylbiphenyl (3)

In this instance the 2-fluoro-4-methylbiphenyl was heated to 140° to 170° C. with a heating mantle and under irradiation with light without a solvent while one equivalent of Br$_2$ was added dropwise. Subsequent NMR analysis showed the starting material:monobromide:dibromide ratio to be 25:58:18.

EXAMPLE 8

Preparation of 2-(2-fluoro-4-biphenylyl)acetonitrile (4)

The crude monobromide prepared in Example 4 was refluxed with 100 ml of EtOH and 6.9 g (0.14 mol) of NaCN for one hour. Most of the EtOH was then removed in a rotary evaporator at reduced pressure and the resulting residue was partitioned between H$_2$O and Et$_2$O. The Et$_2$O phase was dried over MgSO$_4$ and concentrated to leave 19.3 g of brown semi-solid material. Analysis of this material by NMR showed that it contained the acetonitrile and only trace amounts of the monobromide. The crude acetonitrile material was stirred all night in petroleum ether and then filtered. The product was collected as 13.2 g of brown solid that contained about 5% of the starting material according to GC analysis. Concentration of the petroleum ether solution gave 4.9 g of orange liquid that contained mostly the starting material and some of the product acetonitrile. The yield of the 95% pure acetonitrile based on unrecovered fluoride (3) was about 70–80%.

EXAMPLE 9

Preparation of 2-(2-fluoro-4-biphenylyl)propionitrile (5)

The crude 2-(2-fluoro-4-biphenylyl)acetonitrile prepared in Example 8 was recrystallized from an ethyl acetate, hexane mixture to give for the first crop of crystals 4.0 g of brown solid, m.p. 75°–78°, and for the second crop of crystals 3.8 g of less pure material that contained some 2-fluoro-4-methylbiphenyl. Concentration of the material from the mother liquor gave 5.0 g of 2-(2-fluoro-4-biphenylyl)acetonitrile which contained about 8% of 2-fluoro-4-methylbiphenyl. To a solution of this latter material (5.0 g, about 24 mmol of nitrile) in 30 ml of diethyl carbonate was added under an atmosphere of nitrogen a solution of NaOEt (prepared from 1.1 g, 48 mmol of Na) in 25 ml of EtOH. The EtOH was distilled from the reaction mixture until a thick paste formed, at which time an additional 25 ml of diethyl carbonate was added until the temperature of the reaction mixture reached 120°. After the addition of another 25 ml of EtOH, the reaction mixture was cooled to about 10° and 6 g (63 mmol) of $CH_3Br$ was added. The reaction mixture was stirred for one hour at 25° during which a precipitate of NaBr was noticed. The reaction mixture was then refluxed for one hour, cooled, and concentrated on a rotary evaporator. The residue was partitioned between $Et_2O$ and dilute aqueous HCl. The $Et_2O$ layer was dried and concentrated to give 10.8 g of brown liquid that consisted mainly of 2-(2-fluoro-4-biphenylyl)propionitrile by NMR and GC analysis.

EXAMPLE 10

Preparation of 2-(2-fluoro-4-biphenylyl)propionitrile (5)

The purified 2-(2-fluoro-4-biphenylyl)acetonitrile described at the beginning of Example 9 (first and second crops of crystals, 7.8 g, 37 mmol) was dissolved in 30 ml of diethyl carbonate, and the solution was heated to 80°. To this solution, a solution of NaOEt (prepared from 1.5 g, 65 mmol of Na in 35 ml of EtOH) was added under an atmosphere of nitrogen. EtOH was then distilled from the reaction mixture while additional diethylcarbonate was added until the temperature of the reaction mixture reached 120°. The reaction mixture was then allowed to cool, and additional EtOH (25 ml) was added. While the temperature of the reaction mixture was 15°, 10 g (100 ml) of $CH_3Br$ was added as a liquid. After the reaction mixture had been stirred for 30 minutes, the temperature had risen to 35° and a light precipitate of NaBr was noticed. Stirring was continued overnight at ambient temperature, and the reaction mixture was then concentrated on a rotary evaporator. After the residue was partitioned between $Et_2O$ and $H_2O$, the organic phase was dried and concentrated to give 10.6 g of dark brown liquid that consisted of approximtely 60% ethyl-2-(2-fluoro-4-biphenyl)-2-cyanopropionate and approximately 40% 2-(2-fluoro-4-biphenylyl)propionitrile by GC and NMR analysis.

EXAMPLE 11

Purification of 2-(2-fluoro-4-biphenylyl)propionitrile (5)

The product obtained in Example 10 was refluxed under $N_2$ with 35 ml of ethanol containing NaOEt (prepared from 1.0 g of Na) for one hour. GC analysis of an aliquot of the reaction mixture showed a very small amount of the cyanopropionate (7). The mixture was then concentrated and the product was isolated with ether to yield 8.6 g of a brown solid. This brown solid was mixed with the product obtained in Example 9 and distilled through a 15 cm Vigreaux Column. After a forerun of 0.6 g which consisted mainly of a mixture of 2-fluoro-4-methylbiphenyl and the propionitrile (5) (65:30 area percent of GC), the propionitrile (5) was collected in two fractions:

Fraction Number 1—B.P. 120° to 124° at 0.07 mm pressure—4.4 g

Fraction Number 2—B.P. 124° to 130° at 0.07 mm pressure—4.7 g

Both fractions solidified and the first was found to have a melting point of 67° to 70° and the second had a melting point of 70° to 73°.

EXAMPLE 12

Preparation of 2-(2-fluoro-4-biphenylyl)propionic acid-Fluorbiprofen (6)

A mixture of 3.8 g (16.9 mmol) of the propionitrile (5) prepared according to the procedure of Example 11 (melting point 69°-72° C.), 3.5 g (87 mmol) of NaOH, 25 ml of $H_2O$ and 25 ml of $CH_3OH$ was allowed to reflux for 16 hours. The resulting clear, colorless solution was acidified with HCl and extracted with $Et_2O$. The resulting $Et_2O$ solution was dried and concentrated to yield 4.0 g (98%) of the propionic acid (6) as a colorless solid having a melting point of 109°-113° C. According to the *Merck Index*, Ninth Edition, 1976, pure Fluorbiprofen melts at 113°-114° C.

EXAMPLE 13

Preparation of Ethyl-2-(2-fluoro-4-biphenylyl)-2-cyanopropionate (7)

To a solution of 4.8 g (23 mmol) of the acetonitrile (4) in 30 ml of $(EtO)_2CO$ was added 3.2 g (46 mmol) of NaOEt under an $N_2$ atmosphere. The reaction mixture was then refluxed for 1.2 hours, the reaction temperature reaching 124°. The mixture was then cooled to 60° and 5.8 g (46 mmol) of $(CH_3)_2SO_4$ was added. This mixture was stirred for 5 minutes and then refluxed for 20 minutes. Upon cooling the mixture was partitioned between $Et_2O$ and $H_2O$. The $Et_2O$ layer was dried over $MgSO_4$ and concentrated at reduced pressure and elevated temperatures. Subsequent NMR analysis of a sample of the residue indicated a mixture of the cyanopropionate (7) and $(EtO)_2CO$ with only a trace of the acetonitrile (4). The remaining residue was distilled through a short path to yield 5.1 g (75%) of a yellow liquid having a boiling point of 160° (at 0.05 mm pressure). NMR indicated a majority of the cyanopropionate (7) and also some minor extraneous peaks.

Although the above examples have shown various modifications and variations of the present invention, other modifications and variations are possible in light of the above teachings. It is therefore to be understood that changes may be made in the particular embodiments of the invention described which are within the full intended scope of the invention.

What is claimed is:

1. A method for the preparation of 2-fluoro-4-monobromomethylbiphenyl which comprises reacting 2-fluoro-4-methylbiphenyl with N-bromosuccinimide or bromine under irradiation with light.

2. A method for the preparation of 2-fluoro-4-monobromomethylbiphenyl which comprises photo-initiating bromination of 2-fluoro-4-methylbiphenyl with N-bromosuccinimde or bromine in refluxing carbon tetrachloride solution.

3. A method for the preparation of 2-fluoro-4-monobromomethylbiphenyl which comprises photo-initiating bromination of 2-fluoro-4-methylbiphenyl with N-bromosuccinimide in solution, the reactants being employed in a molar ratio of about 1.0 to 0.9, respectively.

4. A method for the preparation of 2-fluoro-4-monobromomethylbiphenyl which comprises adding from 0.8 to 1 equivalent of bromine in small portions to a refluxing solution of 2-fluoro-4-methylbiphenyl under irradiation with light.

* * * * *